United States Patent
Cull

(10) Patent No.: US 8,211,056 B2
(45) Date of Patent: Jul. 3, 2012

(54) DEVICES AND METHODS TO FACILITATE CANNULATION OF AN ARTERIOVENOUS FISTULA

(75) Inventor: David L. Cull, Greenville, SC (US)

(73) Assignee: CreatiVasc Medical, LLC, Greenville, SC (US)

( * ) Notice: Subject to any disclaimer, the term of this patent is extended or adjusted under 35 U.S.C. 154(b) by 943 days.

(21) Appl. No.: 12/064,099

(22) PCT Filed: Aug. 22, 2006

(86) PCT No.: PCT/US2006/032991
§ 371 (c)(1),
(2), (4) Date: Jul. 2, 2008

(87) PCT Pub. No.: WO2007/024995
PCT Pub. Date: Mar. 1, 2007

(65) Prior Publication Data
US 2008/0269677 A1     Oct. 30, 2008

Related U.S. Application Data

(60) Provisional application No. 60/710,209, filed on Aug. 22, 2005.

(51) Int. Cl.
*A61M 5/00*     (2006.01)
(52) U.S. Cl. ........................ 604/116; 604/115
(58) Field of Classification Search .......... 604/180, 604/115–117
See application file for complete search history.

(56) References Cited

U.S. PATENT DOCUMENTS

| | | | |
|---|---|---|---|
| 1,991,103 A | 2/1935 | King | |
| 3,324,854 A * | 6/1967 | Weese | 604/115 |
| 4,314,568 A | 2/1982 | Loving | |
| 4,586,924 A | 5/1986 | Lanning | |
| 5,254,095 A | 10/1993 | Harvey | |
| 5,415,647 A | 5/1995 | Pisarik | |
| 5,554,106 A * | 9/1996 | Layman-Spillar et al. | 602/42 |
| 6,066,116 A | 5/2000 | Fox | |
| 6,524,297 B1 | 2/2003 | Newman | |
| 6,652,487 B1 | 11/2003 | Cook | |
| 6,673,091 B1 * | 1/2004 | Shaffer et al. | 606/201 |
| 6,923,762 B1 * | 8/2005 | Creaghan, Jr. | 600/249 |

FOREIGN PATENT DOCUMENTS
CH     242 734     5/1945

OTHER PUBLICATIONS

International Search Report, mailed Jul. 7, 2008—2 pages.
Supplementary Partial European Search Report—3 pages.

* cited by examiner

*Primary Examiner* — Theodore Stigell
(74) *Attorney, Agent, or Firm* — Dority & Manning, P.A.

(57) ABSTRACT

The present disclosure is directed to a device for locating a fistula. The device can include a first tine and a second tine each having a distal end and a proximal end with the first tine spaced a distance from the second tine sufficient for allowing a section of a fistula to fit therebetween. A compression member can be placed adjacent to the first tine and the second tine such that the compression member externally compresses and temporarily occludes a fistula thereby increasing blood pressure in a section of a fistula located between the first tine and the second tine.

20 Claims, 6 Drawing Sheets

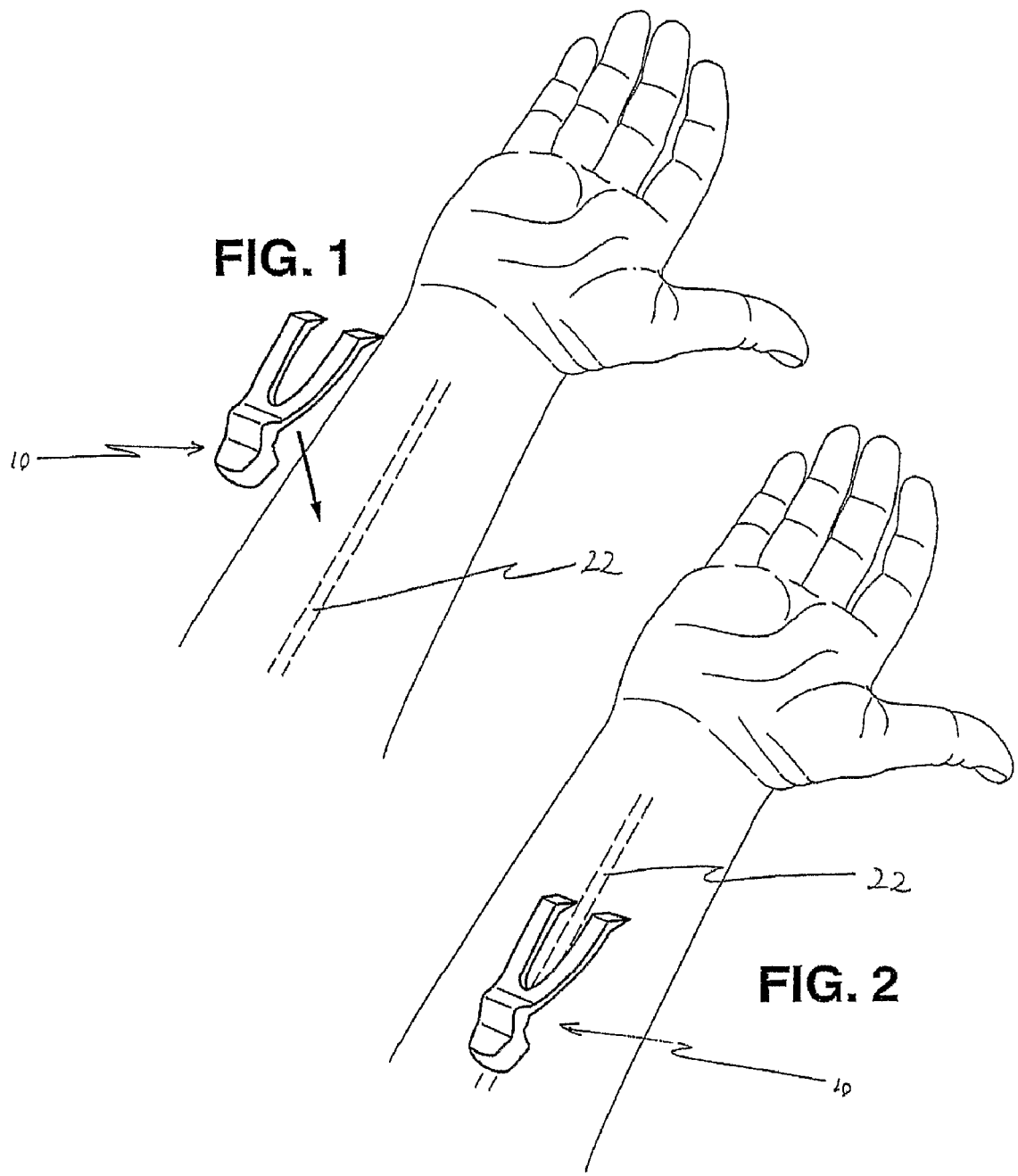

DEVICES AND METHODS TO FACILITATE CANNULATION OF AN ARTERIOVENOUS FISTULA

CROSS REFERENCE TO RELATED APPLICATION

The present application is based on and claims priority to U.S. Provisional Application Ser. No. 60/710,209 having a filing date of Aug. 22, 2005.

BACKGROUND

End-stage renal disease (ESRD) is characterized by a complete or near complete failure of the kidneys to function to excrete wastes, concentrate urine, and regulate electrolytes. In such cases, kidney function is so low that complications are multiple and severe, and death will occur from accumulation of fluids and waste products in the body.

A common life-sustaining treatment for patients with ESRD is hemodialysis. Hemodialysis is a process whereby large amounts of blood are rapidly removed from the body and filtered through a machine that removes wastes and extra fluid. The cleaned blood is then returned back into the body.

An important step before starting regular hemodialysis is preparing a vascular access, which is a site on the body where blood will be removed and returned during dialysis. In this regard, creation of an arteriovenous fistula (AV fistula) is a commonly performed operation in which an artery is connected directly to a vein. The high blood pressure of the artery causes more blood to flow into the vein and, as a result, the vein dilates growing larger and stronger.

However, to connect the patient to a dialysis machine, a nurse or some other medical technician must insert a large gauge needle through the skin into the AV fistula. The technique of cannulating an AV fistula for dialysis requires considerable skill. The AV fistula often lies several centimeters below the surface of the skin and cannot be located by visual inspection. A medical technician is forced to locate the AV fistula by palpation. Since resistance to blood flow in the vein is low, a pulse is usually not present in the AV fistula. The tactile clue utilized to locate the AV fistula is a vibration caused by turbulent blood flow in the vein. The medical technician tries to identify the location of maximum vibration on the surface of the skin with his/her fingertip to identify the location of the underlying AV fistula in order to cannulate it. If the medical technician is unable to properly identify the correct location of the AV fistula, the dialysis needle may inadvertently puncture the side rather than the center of the AV fistula and result in damage and significant bleeding or thrombosis of the AV fistula. Thus, a need exists for a device and method that can simplify the technique of AV fistula cannulation.

SUMMARY

Objects and advantages of the invention will be set forth in part in the following description, or may be obvious from the description, or may be learned through practice of the invention.

The present disclosure is directed to a device for locating a fistula. The device can include a first tine and a second tine each having a distal end and a proximal end with the first tine spaced a distance from the second tine sufficient for allowing a section of a fistula to fit therebetween. A compression member can be placed adjacent to the first tine and the second tine such that the compression member externally compresses and temporarily occludes a fistula thereby increasing blood pressure in a section of a fistula located between the first tine and the second tine.

In certain embodiments of the device, the first tine and the second tine may be connected together at each proximal end. The first tine and the second tine may be connected together at each proximal end and each distal end such that they generally form an o-shape. The first tine and the second tine may be pivotally connected together at their proximal ends such that the distance between the first tine and the second tine is adjustable. The first tine and the second tine may be formed from a malleable material such that the distance between the first tine and the second tine is adjustable. The compression member may be integrally connected with the first tine and the second tine. The compression member may be attached to the first tine and the second tine. The compression member may be formed from the same material as the first tine and the second tine. The compression member, first tine, and second tine may be formed from plastic. The compression member, first tine, and second tine may be formed from a material having antibacterial properties.

In another embodiment of the present disclosure, a device for locating a fistula is disclosed. The device can include a first tine and a second tine each having a distal end and a proximal end and the first tine and a second tine being integrally connected together at each proximal end, the first tine spaced a distance from the second tine sufficient for allowing a section of a fistula to fit therebetween. A compression member can be integrally connected with the first tine and second tine such that the compression member externally compresses and temporarily occludes a fistula thereby increasing blood pressure in a section of a fistula located between the first tine and the second tine.

In still another embodiment of the present disclosure, a method for locating a fistula is disclosed. The method includes providing a device having a first tine, a second tine, and a compression member, positioning the first tine and the second tine a distance sufficient for allowing a section of a fistula to fit therebetween, positioning the compression member adjacent to the first tine and the second tine such that the compression member externally compresses and temporarily occludes a fistula thereby increasing blood pressure in a section of a fistula located between the first tine and said the tine.

Other features and aspects of the present disclosure are discussed in greater detail below.

DESCRIPTION OF THE DRAWINGS

A full and enabling disclosure, including the best mode thereof to one of ordinary skill in the art, is set forth more particularly in the remainder of the specification, including reference to the accompanying figures in which:

FIGS. 1-4 illustrate successive steps of positioning and operating a device to locate and cannulate a fistula in accordance with one embodiment of the present disclosure;

FIG. 7 is a cross-sectional view taken along line 7-7 of FIG. 5; and

FIG. 9 is a cross-sectional view taken along line 9-9 of FIG. 8.

DETAILED DESCRIPTION

It is to be understood by one of ordinary skill in the art that the present discussion is a description of exemplary embodiments only, and is not intended as limiting the broader aspects of the present invention, which broader aspects are embodied in the exemplary construction.

In general, the present disclosure is directed to devices and methods to facilitate cannulation of an arteriovenous (AV) fistula. In particular, the devices and methods described herein greatly simplify the technique of arteriovenous fistula cannulation by improving a technician's ability to locate a fistula.

Very generally, a fistula is a connection between two parts of the body that are usually separate. An AV fistula is useful because it allows for easy access to the blood system of a patient. Creation of an AV fistula is a commonly performed operation in which an artery is connected directly to a vein. The high blood pressure of the artery causes more blood to flow into the vein and, as a result, the vein dilates growing larger and stronger. An AV fistula is considered the best long-term vascular access for hemodialysis because it provides adequate blood flow for dialysis, lasts a long time, and has a complication rate lower than other types of access. When cannulated correctly, a properly formed AV fistula is less likely than other kinds of vascular accesses to form clots or become infected. Also, AV fistulas tend to last many years, longer than any other kind of vascular access.

However, once an AV fistula is formed, the tactile clue that a technician uses to locate it (a vibration caused by turbulent blood flow in the vein) is difficult to locate at best. A technician tries to identify the location of maximum vibration on the surface of the skin with his/her fingertip to identify the location of the underlying fistula in order to cannulate it. The present devices and methods enhance a technician's ability to locate an AV fistula by transforming the tactile clue the technician uses to locate the AV fistula from a vibration to a pulse.

Figure 5:
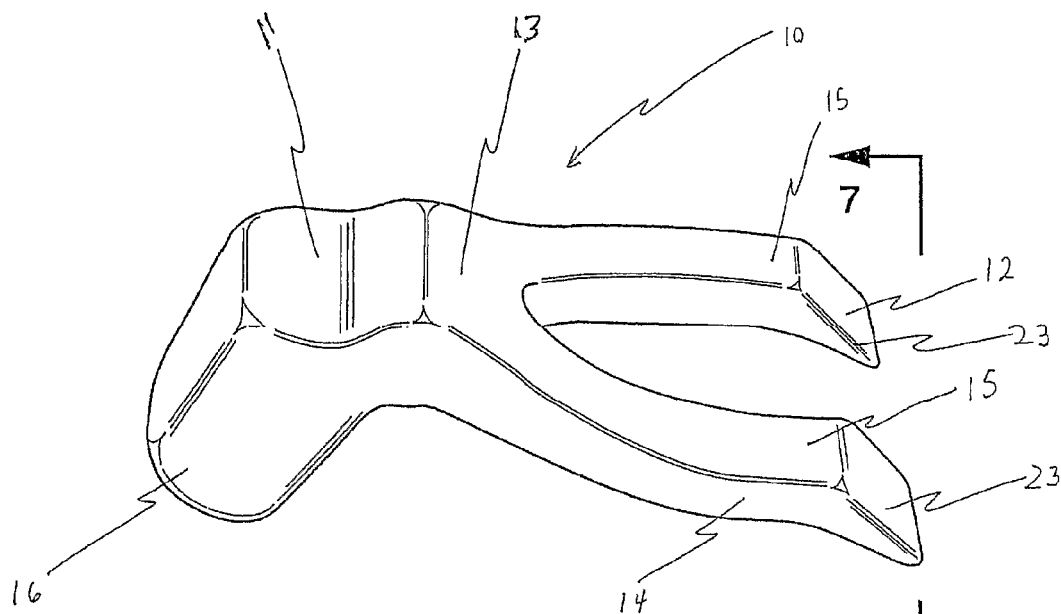
FIGS. 5-9 depict a device to locate a fistula in accordance with one embodiment of the present disclosure.
Figure 6:
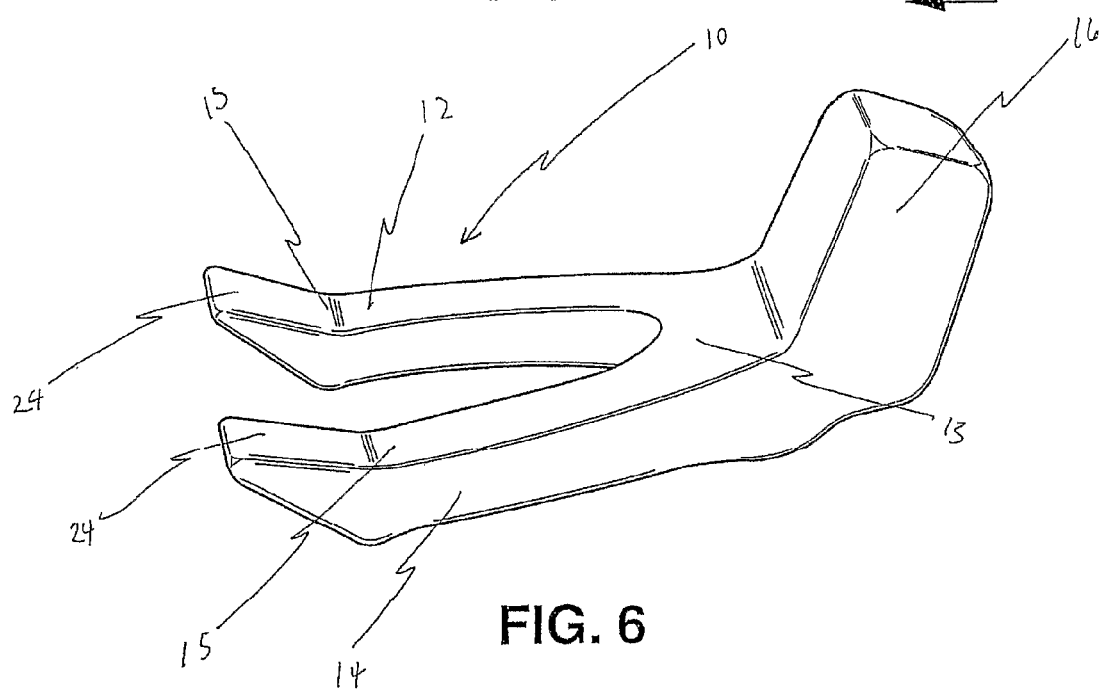
Figure 7:
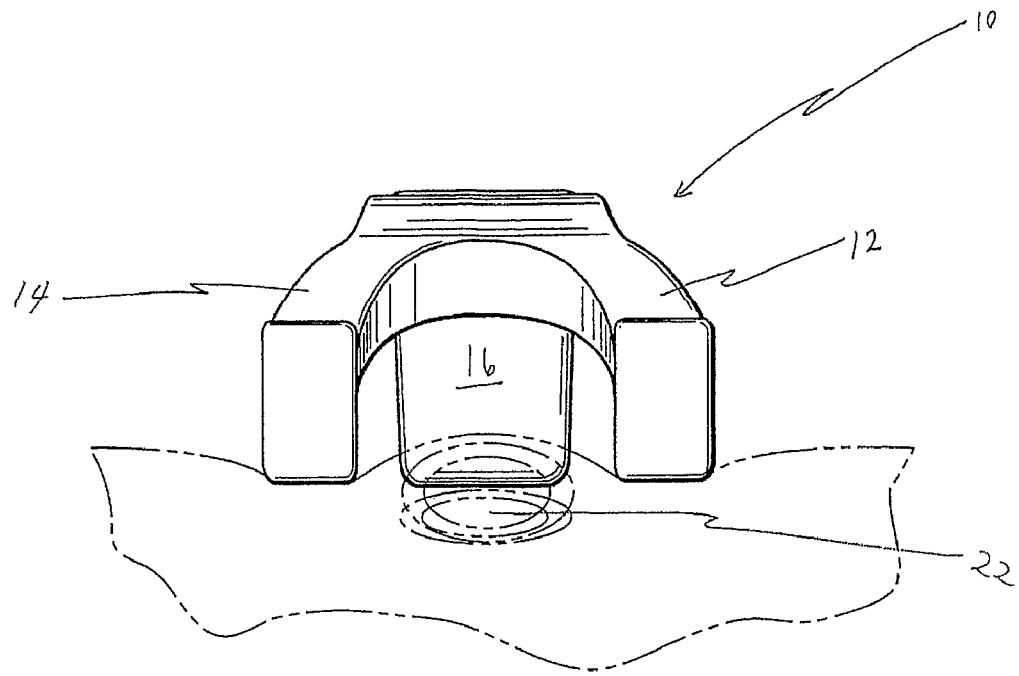

Referring now to FIGS. 5-7, a fistula-locating device 10 in accordance with one embodiment of the present disclosure is shown. The fistula-locating device 10 comprises two tines 12, 14 and a compression member 16.

The two tines 12, 14 are generally equal in length and width. The two tines 12, 14 can be formed from any suitable material known in the art such as a type of plastic material, an elastomeric material, or a metal. In some embodiments, the two tines 12, 14 can be formed from a suitable material that has antibacterial properties.

In some embodiments, the two tines 12, 14 each have a proximal end 13 and a distal end 15. The two tines 12, 14 are positioned such that they are joined at their proximal end 13. The distal end 15 of each tine 12, 14 can include a projecting member defining a top surface 23 and a contact surface 24. The contact surface 24 projects downward at a slant and can form an edge that contacts the patient.

In some embodiments, the two tines 12, 14 are positioned adjacent to one another and connected such that together they generally form a u-shape or v-shape. In other embodiments, the two tines 12, 14 can be connected at their distal end 15 as well such that they generally form an o-shape.

The two tines 12, 14 should be positioned a sufficient distance apart so as to allow a section of AV fistula to fit therebetween. In some embodiments, at least a portion of the distal ends 15 of the two tines 12, 14 are spaced between about 1 to 4 cm apart. In accordance with the present disclosure, however, at least a portion of the two tines 12, 14 should be spaced a sufficient distance apart to allow for a section of AV fistula 22 to fit therebetween.

Figure 8:
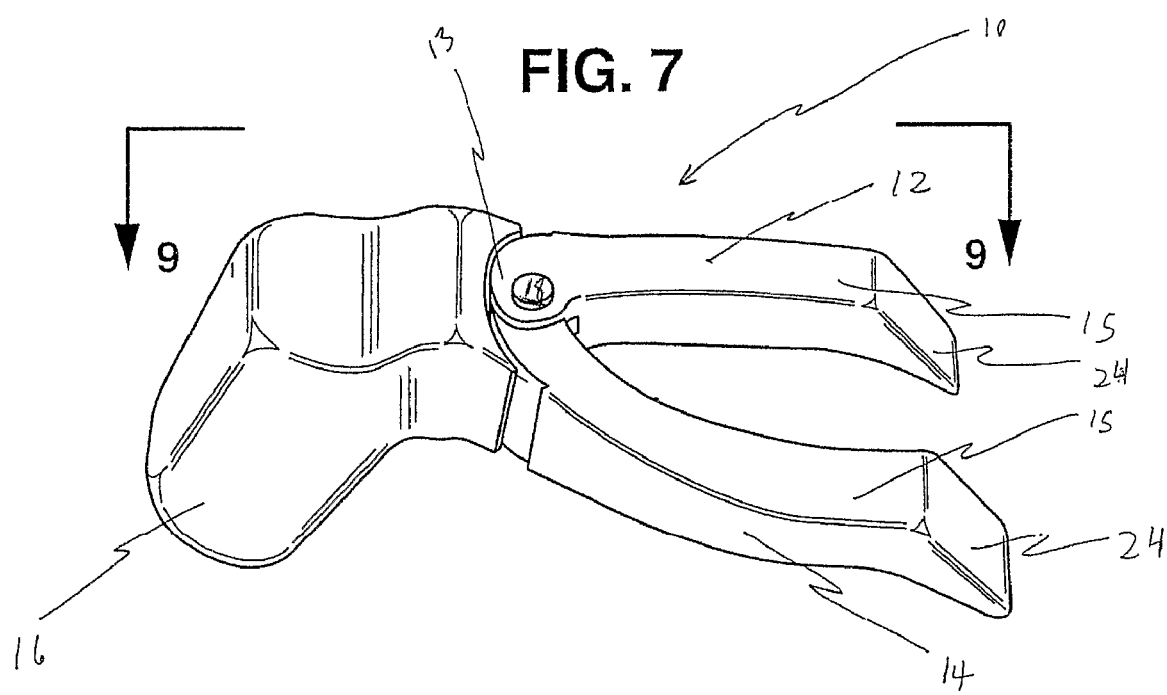
Figure 9:
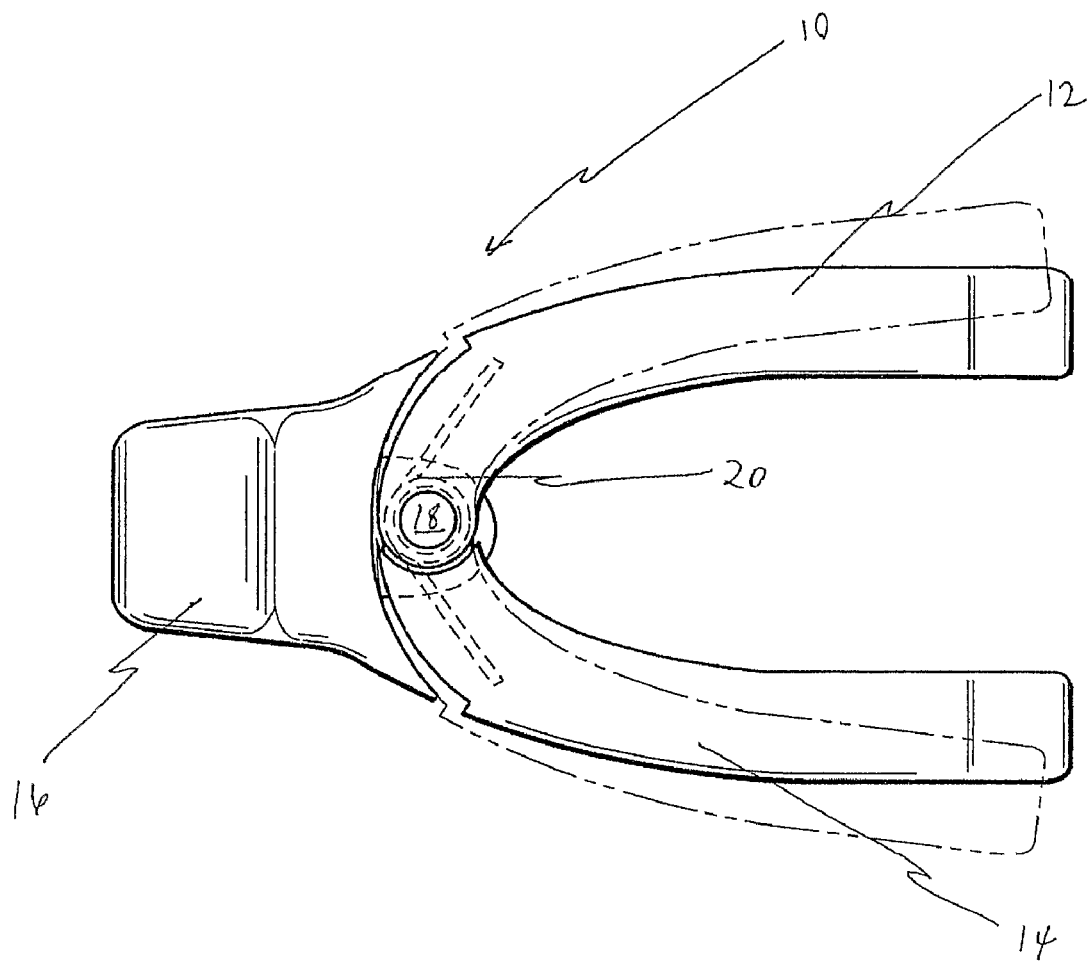

Referring to FIGS. 5 and 6, in some embodiments the two tines 12, 14 can be integrally connected together. With reference to FIGS. 8 and 9, in some embodiments the two tines 12, 14 can be connected together by a pin 18 such that the distance between the two tines 12, 14 can be adjusted. In such embodiments, the pin 18 can be connected to a spring 20 so that the two tines 12, 14 return to their initial position after adjustment. Such embodiments allow a technician to decrease the distance between the tines 12, 14 to accommodate a smaller AV fistula 22. In still other embodiments, the two tines 12, 14 are connected together by attachment methods as would be known to one of ordinary skill in the art. Examples of such attachment methods include adhesives, mechanical fastening, and the like.

In other embodiments, the distance between the two tines 12, 14 can be adjustable by other means. For example, in some embodiments, the two tines 12, 14 can be formed from a malleable material in which the distance between the two tines 12, 14 can be adjusted a sufficient distance to allow a section of AV fistula 22 to fit therebetween.

The fistula-locating device 10 also comprises a compression member 16. In some embodiments, the compression member 16 has a generally rectangular shape. The compression member 16 should be of sufficient length and width so as to externally compress and temporarily occlude an AV fistula 22. The compression member 16 can be formed from the same material as the two tines 12, 14. However, the compression member 16 can be formed from any suitable material known in the art such as a plastic or metal. In some embodiments, the compression member 16 can be formed from a suitable material that has antibacterial properties.

In some other embodiments, the compression member 16 is integrally connected to the tines 12, 14. In some embodiments, the compression member 16 extends below the tines 12, 14 at an angle from a plane defined by the top surfaces 23 of the tines 12, 14. In still other embodiments, the compression member 16 is slanted at an angle ranging from between about 60 to 90 degrees from the plane defined by the top surfaces 23 of the two tines 12, 14.

In some embodiments, the compression member 16 is connected to the tines 12, 14 by attachment methods as would be known to one of ordinary skill in the art. Examples of such attachment methods include adhesives, mechanical fastening, and the like. In still other embodiments, the compression member 16 is not connected to the tines 12, 14 at all.

In some embodiments, the compression member can include an indention 11. Indention 11 allows a technician to more easily grip the compression member 16 to externally compress and temporarily occlude the AV fistula 22.

Referring now to FIGS. 1-4, the use of the device 10 for locating an AV fistula 22 will be described in detail. Referring now in particular to FIGS. 1 and 2, an embodiment of the device 10 is positioned externally above the general location of the AV fistula 22. The device 10 is positioned such that the compression member 16 is placed generally above the AV fistula 22 distal to the arterial anastomosis (surgical union of the artery and vein). The contact surfaces 24 of the device 10 project downward at a slant and form an edge that contacts the patient.

Figure 3:
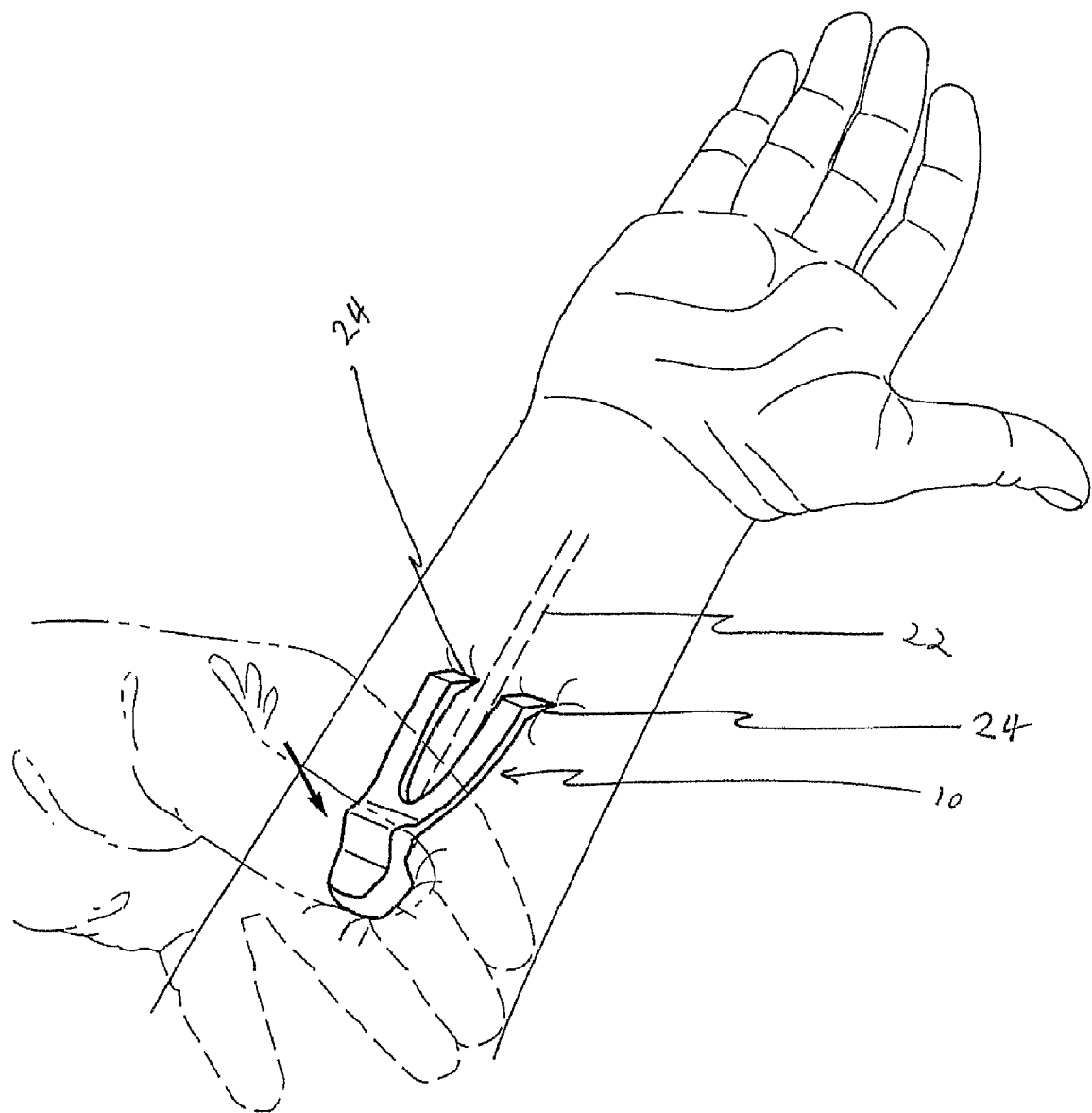
Figure 4:
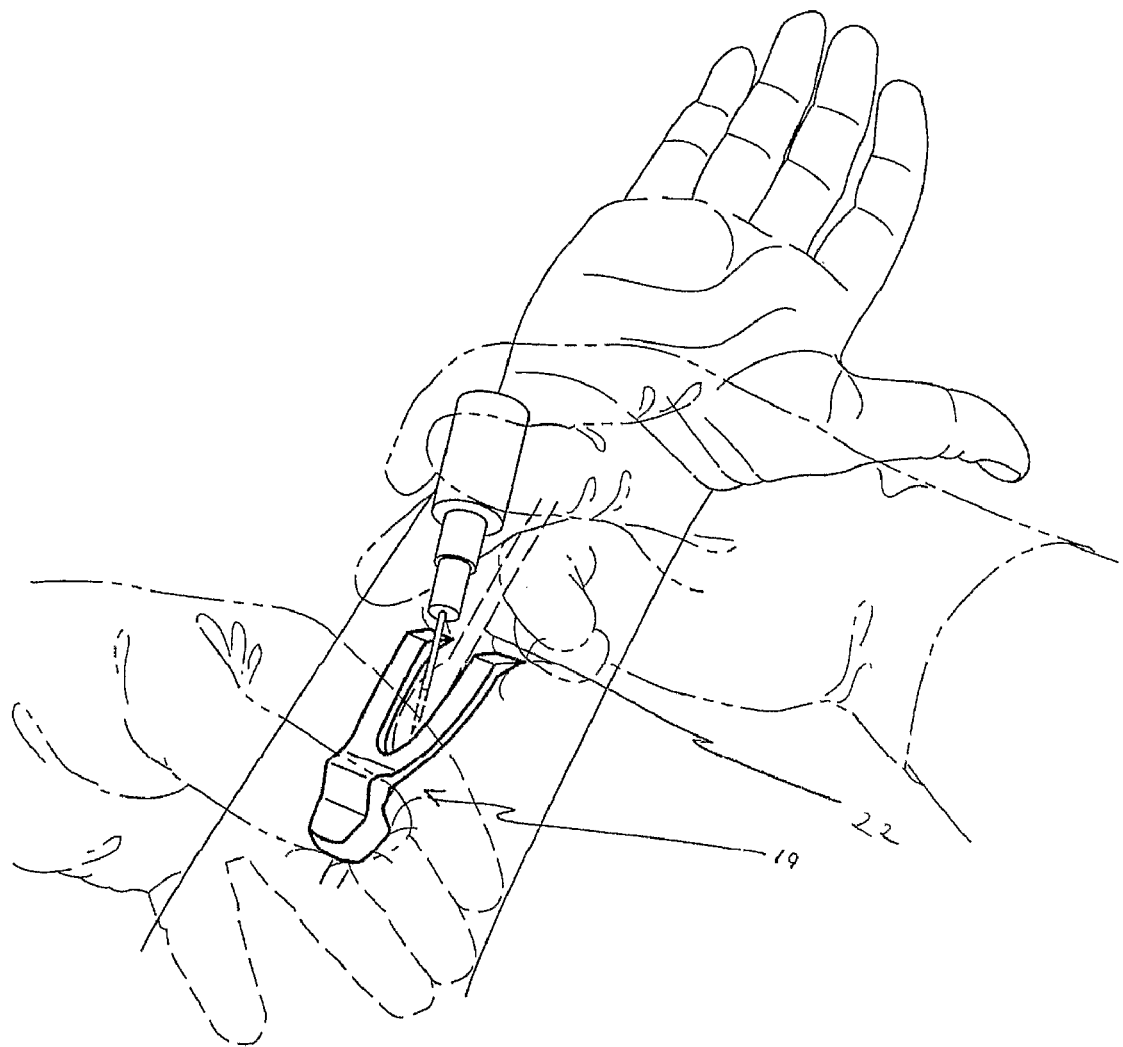

As illustrated in FIG. 3, once the device 10 is properly positioned, a technician compresses the compression member 16 so as to externally compress and temporarily occlude the AV fistula 22. Blood flow restriction through the AV fistula 22 caused by the compression member will result in distention of the fistula between the two tines 12, 14 and will convert a vibration in the AV fistula 22 into a pulse which can be easily detected between the two tines 12, 14. As a result, referring to FIG. 4, a technician is able to simply insert a needle between the two tines 12, 14 of the device 10.

The tines 12, 14 mark the lateral borders of the AV fistula 22, which provides a visual clue to a technician with regards to the location of the AV fistula 22. In addition, the increased blood pressure in the AV fistula 22 caused by the compression member 16 causes the AV fistula 22 to dilate, which further facilitates cannulation. In this manner, a technician can easily identify the correct location of the AV fistula and the dialysis needle can be inserted without damage and significant bleeding or thrombosis to the AV fistula 22.

These and other modifications and variations to the present disclosure may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only and is not intended to limit the invention so further described in such appended claims.

What is claimed is:

1. A device for locating a fistula comprising:
a first tine and a second tine, said first tine and said second tine each having a distal end and a proximal end, the distal end of each tine configured to contact skin of a patient, said first tine spaced a distance from said second tine sufficient for allowing a section of a fistula to fit therebetween: and
a compression member, said compression member being integrally connected to said first tine and said second tine at said proximal ends such that said compression member externally compresses and temporarily occludes the fistula thereby increasing blood pressure in a section of the fistula located between said first tine and said second tine,
wherein said compression member is oriented relative to said first and second tines such that only a portion of said first and second tines contact skin adjacent to the fistula when the compression member externally compresses and temporarily occludes the fistula.

2. The device of claim 1, wherein said first tine and said second tine are connected together at each said proximal end.

3. The device of claim 1, wherein said first tine and said second tine are pivotally connected together at their proximal ends such that the distance between said first tine and said second tine is adjustable.

4. The device of claim 1, wherein said first tine and said second tine are formed from a malleable material such that the distance between said first tine and said second tine is adjustable.

5. The device of claim 1, wherein said compression member is integrally connected with said first tine and said second tine.

6. The device of claim 1, wherein said compression member is attached to said first tine and said second tine.

7. The device of claim 1, wherein said compression member, said first tine, and said second tine are formed from a material having antibacterial properties.

8. The, device of claim 1, wherein said compression member extends at an angle from said proximal ends of said first and second tines such that said proximal ends are spaced apart from the skin when the compression member externally compresses and temporarily occludes the fistula.

9. The device of claim 1, wherein only a portion of said distal ends of said first and second tines contacts the skin adjacent to the fistula when the compression member externally compresses and temporarily occludes the fistula.

10. The device of claim 1, wherein said compression member is oriented relative to said first and second tines such that it extends below said first and second tines at an angle ranging from about 60 to 90 degrees from a plane defined by a top surface of said first tine and said second tine.

11. A device for locating a fistula comprising:
a first tine and a second fine, said first tine and said second tine each having a distal end and a proximal end, the distal end of each tine configured to contact skin of a patient, said first tine and said second tine being integrally connected together at each said proximal end, said first fine spaced a distance from said second tine sufficient for allowing a section of a fistula to fit therebetween; and
a compression member, said compression member being integrally connected with said first tine and said second tine at said proximal ends such that said compression member externally compresses and temporarily occludes a fistula thereby increasing blood pressure in a section of a fistula located between said first tine and said second tine,
wherein said compression member is oriented such that it extends below said first and second tines at an angle from a plane defined by a top surface of said first tine and said second tine.

12. The device of claim 11, wherein said angle ranges from about 60 to 90 degrees.

13. The device of claim 11, wherein said first tine and said second tine are adjustably spaced from about 1 to 4 cm apart.

14. The device of claim 11, wherein said compression member, said first tine, and said second tine are formed from a material having antibacterial properties.

15. A method for locating a fistula with a device including a first tine, a second tine and a compression member, said tines each having a distal end and a proximal end, the distal ends configured to contact skin of a patient, said compression member being integrally connected with said first tine and said second tine at said proximal ends, the method comprising:
positioning said first tine and said second tine such that a section of a fistula is aligned therebetween;
compressing said compression member such that said compression member externally compresses and temporarily occludes the fistula thereby increasing blood pressure in a section of the fistula located between said first tine and said second tine; and
contacting only a portion of said first and second tines against skin adjacent to the fistula as the compression member is compressed.

16. The method of claim 15, further comprises inserting a dialysis needle in said fistula.

17. The method of claim 15, wherein said first tine and said second tine are adjustably spaced from about 1 to 4 cm apart.

18. The method of claim 15, wherein said compression member, said first tine, and said second tine are formed from a material having antibacterial properties.

19. The method of claim 15, wherein contacting only a portion of said first and second tines against skin adjacent to the fistula as the compression member is compressed comprises contacting only a portion of a distal end of said first and second tines as the compression member is compressed.

20. The method of claim 15, wherein said compression member is oriented relative to said first and second tines such that it extends below said first and second tines at an angle ranging from about 60 to 90 degrees from a plane defined by a top surface of said first tine and said second tine.

* * * * *